United States Patent [19]
Chavkin et al.

[11] Patent Number: 5,753,255
[45] Date of Patent: May 19, 1998

[54] CHEWABLE MOLDED TABLET CONTAINING MEDICINALLY ACTIVE SUBSTANCES

[76] Inventors: Leonard Chavkin, 704 Warren Glen Rd., Bloomsbury, N.J. 08804; Leonard Mackles, 311 E. 23rd St., New York, N.Y. 10010

[21] Appl. No.: 795,472

[22] Filed: Feb. 11, 1997

[51] Int. Cl.⁶ .................................................. A61K 9/20
[52] U.S. Cl. .................. 424/441; 424/465; 514/785; 514/786; 514/961
[58] Field of Search .................... 424/441, 465; 514/785, 786, 961

[56] References Cited

U.S. PATENT DOCUMENTS 5,037,319  8/1991  Gottwald et al. ............... 424/441

FOREIGN PATENT DOCUMENTS 50-157517  12/1975  Japan.

OTHER PUBLICATIONS

Caplus AN 1976:140735 (Abstract of JP 50-157517).
Caplus AN 1983:410812 (Abstract of Rogaska–Mascher et al., Farm. Pol. (1983) 39(1), 25–8.

*Primary Examiner*—Mark Nagumo
*Attorney, Agent, or Firm*—Omri M. Behr, Esq.

[57] ABSTRACT

There is provided a chewable medicinal tableting composition comprising as proportions of the total composition which will further comprise the medicinally active component, as first essential component: capric triglyceride: about 30 to about 95% by weight, and as second essential component: the medicinally active ingredient: up to 60% by weight. Where the medicinally active ingrdient is less than about 30% by weight the composition further comprises as third essential component, a member of the group consisting of glyceryl monostearate, a mixture of glyceryl monostearate and glyceryl monopalmitate, and a mixture comprising at least about 40–50% by weight of glyceryl monostearate, and glyceryl distearate: up to 10% by weight. There are also disclosed methods of making these compositions.

12 Claims, No Drawings

CHEWABLE MOLDED TABLET CONTAINING MEDICINALLY ACTIVE SUBSTANCES

DISCUSSION OF THE PRIOR ART

Chewable dosage forms for drug delivery are well known to pharmaceutical technology. They are useful for the administration of medication to people particularly children who have trouble swallowing tablets or capsules; or where liquids are inappropriate for drug stability reasons or where patient compliance is a problem among people who reject liquids for reasons of taste or convenience.

Conventional chewable compressed tablets consist of the medicinal agent dispersed in a base composed of sugars, e.g. sucrose, and containing flavors and sweeteners to make the form palatable. Sugarless versions of chewable tablets can be prepared using solid polyols such as Sorbitol, Mannitol or Xylitol and these have found considerable consumer acceptance.

There are some drawbacks or negatives associated with these conventional chewable dosage forms. Some are so hard that they are difficult to chew, some are gritty or chalky tasting, and some do not do an adequate job of masking the taste or texture of the medicinal agents they deliver.

Efforts have been made to provide a more palatable chewable tablet and these have some value. Chapura U.S. Pat. No. (4,786,502), for example, utilizes lipid material to mask bad tasting drugs in chewable form. Morris U.S. Pat. No. (4,609,543) similarly employs lipid material and a special process to provide intimate contact of the lipid with the medicament to achieve superior taste masking. Sharma U.S. Pat. No. (4,894,233) coats the medicament particles with a hydrophobic matrix to mask the taste of the drug. Kehoe U.S. Pat. No. (4,975,270) uses elastomer-encased active ingredients dispersed in an intensely flavored chewing gum base to mask the taste of medicaments.

Among the above-cited references, Chapura U.S. Pat. No. (4,786,502) is the closest to the technology that underlies our invention. His base is a lipid material with a melting point of about 33° C., which melts sharply—similar to cocoa butter. Since such lipids leave a greasy taste sensation in the mouth, he employs dispersant material at levels of 10–50% as an essential ingredient to modify and reduce this unpleasant greasiness. Sugars are his preferred dispersants.

Since dispersants alone do not do an adequate job of reducing greasiness, another essential component of his invention is an emulsifier. He prefers a combination of a low HLB emulsifier with a high HLB emulsifier averaging a final HLB between 8 and 10. This hydrophilic surfactant system helps to disperse the lipid base in saliva and reduce its greasiness in the mouth when chewed. It would therefore be desirable to provided a base having the low melting qualities of Chapura without the greasy mouth feel or need for emulsifier and or dispersing agent.

SUMMARY OF THE INVENTION

Commercially available mixtures of the triglycerides of capric and caprylic acids are liquid at ambient temperatures as is the triglyceride of caprylic acid. However, tricaprin (capric triglyceride) is a structured (manufactured) lipid material prepared by re-esterification of high purity fatty acid (specifically capric or decanoic) acid and glycerin. It has a very sharp melting point in the range of 29°–31° C. and as such is similar to cocoa butter and its substitutes (hydrogenated vegetable oils), but unlike these lipids it has a very unique mouthfeel.

Capric triglyceride (tricaprin) belongs to a family of structured lipids, sometimes called medium chain triglycerides. Although these are lipids, being triesters of edible fatty acids and glycerin, they do not behave like conventional triesters of the higher edible fatty acids and glycerin. For example, they are not metabolized by the human digestive tract in the ordinary manner of fats. They are absorbed directly into the portal circulation and are metabolized like glucose for energy rather than deposited as body fat.

They also have different physical characteristics than ordinary fats, such as lower viscosities, solubility in alcohol, no greasy feel on the skin, and as such find special usefulness in the pharmaceutical and cosmetics and toiletries industries. However, due to its relatively high melting point, tricaprin can be used in solid compositions in contrast to the aforementioned mixed triglyceride or caprylic triglyceride.

The present invention discloses a lipid material system that within itself has the properties to produce the desired mouth dispersibility and requires no dispersant material and no emulsifier to produce a superior tasting chewable tablet.

When chewed, a molded tablet made with tricaprin as the fatty base, melts almost instantly in the mouth and leaves no greasy feel in the mouth or on the lips. Additionally, its negative heat of fusion produces a very pleasant cooling sensation as it melts.

The basic ingredients of the present invention are tricaprin and the medicinal agent. Thus, for example, it is feasible to make a molded chewable antacid tablet with equal parts of powdered calcium carbonate and tricaprin.

However, when tricaprin is molded with small amounts of a medicinal agent, it does not crystallize easily or rapidly to produce a smooth uniform tablet. Instead, after a prolonged period of cooling at 15°–20° C., it crystallizes into a lumpy, grainy mass that crumbles easily when handled (as in packaging or shipping).

In these circumstances, it is desirable to provide a tempering or solidifying agent that serves two functions, first to speed the solidification of the molded tablet and secondly, to produce a smooth, hard tablet that does not crumble when handled. Such an additive must be effective at very low concentrations so that the basic benefit of the tricaprin, i.e., its rapid melting, non-greasy cooling taste is maintained.

Many lipid and waxy materials with melting points in the range of 55°–75° C. have been considered as possible tempering agents. For example, stearic acid, stearyl alcohol, sorbitan monostearate, hydrogenated vegetable oils, hydrogenated castor oil (castor wax) are all considered potentially useful but substantially inoperative as effective tempering agents at low concentrations (less than 5% of the amount of tricaprin present). When each of the above-cited materials was added to tricaprin at 5% of the amount of tricaprin present and the mixture was allowed to solidify by cooling at 15°–20° C. the resulting tablet was lumpy, brittle, crumbled when handled and was not smooth and homogeneous.

The material that which has been found to meet the criteria for an effective tempering and solidifying agent for tricaprin is commercial glyceryl monostearate (monostearin), also known as monostearin.

DESCRIPTION OF THE PREFERRED EMBODIMENTS

In order to make the most elegant chewable molded tablet of this invention, two components are essential. First, the structured lipid tricaprin is required as the basic forming agent for the tablet. It can be present in amounts ranging from about 30% to more than 95% by weight of the total composition depending upon the amount of the active ingredient present in each tablet.

The second essential component is the medicinally active ingredient of the tablet. The concentration of active will depend upon the dose of the ingredient desired to be present in each tablet and can range from less than one percent by weight of the total as for potent drugs, to about sixty percent of the total weight as in the case of antacids or nutritional supplements.

In the latter situation where the medicinally active ingredient constitutes from about 30% to about 60% of total weight no modifying agent is needed. We have prepared five gram molded tablets of this composition wherein each tablet provides 2.5 grams of calcium carbonate with an acid consuming power of 50 milliequivalent of 0.1N HCl; and each tablet also provides one gram of elemental calcium as a nutritional supplement.

Where the medicinal loading is lower such an agent constitutes the third essential ingredient. The preferred tempering agent commercially glyceryl monostearate (monostearin) is necessary to modify the crystallization characteristics of the tricaprin so that a smooth hard, homogeneous, rapidly solidifying tablet can be molded. The amount of monostearin present is in the range of about 1 to about 5 percent of the amount of tricaprin present, preferably about 2 to 4%.

Monostearin is described in the Merck Index as a mixture of variable proportions of glyceryl monostearate and glyceryl monopalmitate. It is available commercially under a variety of trade names, e.g. Witconol MST (Witco), Tegin (Goldschmidt), Kessco (Armak), Lexemul (Inolex), Atmul (ICI), Aldo (Glyco), Cutina (Henkel) and others. Pure glyceryl monostearate may also be used, however it is not generally available at commercially feasible prices.

Other esters containing glyceryl monostearate can also be used as tempering agents. There are many commercially available mixed esters referred to as mixed mono and diglyceride emulsifiers used mainly as food emulsifiers. These usually contain a minimum of about 40–50% monoester (glyceryl monostearate), have a melting point around 60° C., and an HLB in the range of 2.8–3.5.

Although their use will produce a good molded tablet, their variable composition results in tablets that are not as reliably perfect as when monostearin is used. Since these mixed esters, made from animal fats, may contain some oleic acid esters, their taste is not as clean as that where the glyceryl monoesters, pure stearic acid or of a mixture of stearic and palmitic acid are used.

When monostearin and tricaprin are melted together and molded into tablets, the result is smooth, uniform, and yields rapid solidification into hard homogeneous tablets that break with a snap and sharp fracture without crumbling.

At relatively high concentrations of monostearin (10–20% of the amount of tricaprin) the resulting tablet has a fatty, waxy mouthfeel when chewed. At lower concentrations of monostearin, this fatty taste disappears and the desirable mouthfeel characteristics of the tricaprin predominate.

It is preferred to maintain the concentration of monostearin below 10% by weight of tricaprin such as about 5% of the tricaprin, above which the resultant tablet exhibits some fatty taste and below which this fatty taste is not discernible. Surprisingly, the monostearin exhibits its desirable tempering and hardening effects at concentrations as low as 1% of the amount of tricaprin present.

Even at the extremes of this broad range of concentrations it is possible to mold tablets that exhibit the desired elegant taste and mouthfeel properties that characterize the tablets of this invention. Essentially, when chewed, these tablets behave like liquids.

The usual optional ingredients present in all chewable or liquid pharmaceutical dosage forms can be incorporated into the basic system of this invention. These includes natural and artificial sweeteners, colors, flavors, preservatives, suspending agents, buffers, stabilizing agents, and other ingredients familiar to those skilled in the art of pharmaceutical formulation.

The manufacture of the tablets of this invention is simple and conventional. The lipid ingredients are heated together to melt them with mixing to assure homogeneity at about 60°–70° C. Then the other formulation ingredients are added sequentially, with mixing after each addition to assure uniform dispersion. Flavors are added as the mixture cools to below 50° C. When the mixture is uniform, it is poured into molds of the desired size and shape and cooled to the desired hardness. The tablets can be molded into the final package or molded in bulk and packaged subsequently. If desired, the tablets can be coated by conventional means such as sugar coating or film coating.

|  | % W/W |
|---|---|
| Example 1 Calcium Tablet | |
| Calcium Carbonate | 50.0 |
| Aspartame | 0.2 |
| Saccharin | 0.1 |
| Flavor | 0.1 |
| Tricaprin | 48.6 |
| Monstearin | 1.0 |
| | 100.0% |
| Mold into tablets weighing 5 grams each. Example 2 Cough Cold Tablet | |
| Dextromethorphan | 0.1 |
| Phenylpropanolamine | 0.125 |
| Saccharin | 0.1 |
| Citric Acid | 0.5 |
| Flavor | 0.4 |
| Tricaprin | 95.725 |
| Monostearin | 3.0 |
| D&C Red 27 Lake | 0.05 |
| | 100.000% |
| Example 3 Sore Throat Tablet | |
| Dyclonine HCl | 1.0 |
| Sucrose | 20.0 |
| Cab-O-Sil M5 | 1.0 |
| Flavor | 0.5 |
| Tricaprin | 74.45 |
| D&C Red 27 Lake | 0.05 |
| Monostearin | 3.0 |
| | 100.00% |

We claim:

1. A chewable medicinal molding tableting composition comprising, as proportions of the total composition which will further comprise the medicinally active component, as first essential component: capric triglyceride: about 30 to about 95% by weight, as second essential component: the medicinally active ingredient: up to 60% by weight and as third essential component, a member of the group consisting of glyceryl monostearate, a mixture of glyceryl monostearate and glyceryl monopalmitate, and a mixture comprising at least about 40–50% by weight of glyceryl monostearate, and glyceryl distearate: 1 to 10% of capric triglyceride by weight.

2. The composition of claim 1 wherein the third component is a mixture of glyceryl monostearate and glyceryl monopalmitate.

3. The composition of claim 1 wherein the third component is present in the range of from about 1 to about 5% by weight of the said first component.

4. The composition of claim 3 wherein the third component is present in the range of from about 2 to about 4% by weight of the said first component.

5. A chewable medicinal molded tablet comprising, as proportions of the total composition, as first essential component: capric triglyceride: about 30 to about 95% by weight, as second essential component: the medicinally active ingredient: up to 60% by weight, and as third essential component: a member of the group consisting of glyceryl monostearate, a mixture of glyceryl monostearate and glyceryl monopalmitate, and a mixture comprising at least about 40–50% by weight of glyceryl monostearate and glyceryl distearate: 1 to 10% of capric triglyceride by weight.

6. The tablet of claim 5 wherein the third component is present in the range of from about 1 to about 5% by weight of the said first component.

7. The tablet of claim 6 wherein the third component is present in the range of from 2 to about 4% by weight of the said first component.

8. A method of making a chewable molded medicinal tablet comprising as proportions of the total composition as first essential component: capric triglyceride: about 30 to about 95% by weight, as second essential component: the medicinally active ingredient: up to 60% by weight, and as third essential component: a member of the group consisting of glyceryl monostearate, a mixture of glyceryl monostearate and glyceryl monopalmitate, and a mixture comprising at least about 40–50% by weight of glyceryl monostearate and glyceryl disparate: 1 to 10% of capric triglyceride by weight which comprises heating said first and said second components together to about 60° to about 70° C. to melt, mixing to obtain homogeneity and adding said medicinally active component to form a mixed melt, pouring said mix melt into molds and cooling.

9. The method of claim 8 additionally comprising the steps of adding amd homogeneously mixing in further components sequentially after the medicinally active component prior to cooling to hardening provided that where flavorants are added they are added above hardening temperature but below 50° C.

10. The method of claim 9 wherein the third component is present in the range of from about 1 to about 5% by weight of the said first component.

11. The method of claim 8 wherein the third component is a mixture of glyceryl monostearate and glyceryl monopalmitate.

12. The method of claim 11 wherein the third component is present in the range of from about 2 to about 4% by weight of the said first component.

* * * * *